United States Patent [19]

Frossard

[11] Patent Number: 4,772,549
[45] Date of Patent: Sep. 20, 1988

[54] POLYMORPHISMS RELATED TO LIPID METABOLISM: APOB, APOCII, APOE, APOAIV

[75] Inventor: Philippe M. Frossard, Palo Alto, Calif.

[73] Assignee: Biotechnology Research Partners, Ltd., Mountain View, Calif.

[21] Appl. No.: 900,593

[22] Filed: Aug. 26, 1986

Related U.S. Application Data

[63] Continuation-in-part of Ser. No. 869,177, May 30, 1986, abandoned, which is a continuation-in-part of Ser. No. 782,663, Sep. 30, 1985, abandoned.

[51] Int. Cl.$^4$ .................. C12Q 1/68; G01N 33/566; C07H 21/00
[52] U.S. Cl. .................. 435/6; 435/810; 436/63; 436/94; 436/501; 436/503; 536/27; 935/11; 935/78; 935/79
[58] Field of Search .................. 435/6, 810; 436/63, 436/94, 501, 503; 536/27; 935/11, 78, 79

[56] References Cited

U.S. PATENT DOCUMENTS 4,623,619 11/1986 Owerbach et al. .................. 435/6

FOREIGN PATENT DOCUMENTS 1186991 3/1982 Canada.

OTHER PUBLICATIONS

Kennell, D. E., "Principles and Practices of Nucleic Acid Hybridization", Davidson & Cohn, ed., Prog. in Nucl. Acid Res. & Mol. Biol. 11, 259–301 (1971).
Wallis, S. C. et al, "The Isolation of a Genomic Clone...", Human Genetics 68, 286–289 (Dec. 84).
Fojo, S. S. et al, "Analysis of the ApoCII Gene...", Biochem. Biophys. Res. Comm. 124(1), 308–313 (10/15/84).
Cohen, T. et al., "DNA Polymorphic Sites in the Human...", Nucleic Acid & Research RFLP Report 14(4), 1924 (2/25/86).
Priestly, L. et al, "RFLP for the Human Apolipoprotein B Gene: III; EcoRV", Nucleic Acid & Res. RFLP Report 13(18), 6791 (9/25/85).
Das, H. K. et al, "Isolation, Characterization, ... Human Apolipoprotein E Gene", J. Biol. Chem 260(10), 6240–6247 (5/25/85).
Mandrup-Poulsen, T. et al, "DNA Sequences...", The Lancet, Feb. 4, 1984, pp. 250–252.
Antonarakis et al., Proc. Natl. Acad. Sci. U.S.A., 79: 137–141 (1982).
Giannelli et al., Lancet, pp. 239–241 (2/4/84).
Grunebaum et al., J. Clin. Invest., 73: 1491–1495 (1984).
Gusella et al., Nature, 306: 234–239 (1983).
Jeffreys, Cell 8 (1979).
Kan and Dozy, Proc. Natl. Acad. Sci. U.S.A., 75 (11): 5631–5635 (1978).
Law et al., Gene, 28: 153–158 (1984).
Phillips, "The Growth Hormone (hGH) Gene and Human Disease" in Recombinant DNA: Application to Human Disease, (Eds. C. T. Gaskey and R. L. White), CSH 1983.
Rotwein et al., Science 213: 117–1120 (1981).
Taylor et al., Nature, 251: 392–393 (1984).
Woo et al., Nature, 306: 151–155 (1983).
Humphries et al., Mol. Bio. Med., 1: 463–471, (1984), "A DNA Polymorphism Adjacent to the Human Apolipoprotein CII Gene".
Priestly, L. et al, Nucleic Acids Research, 13: (18): 6789, (1985), "RLFP for the Human Apolipoprotein B Gene: I; BamHI".
Priestly, L. et al, Nucleic Acids Research, 13: (18): 6790, (1985), "RLFP for the Human Apolipoprotein B Gene: II: EcoRI".
Priestly, L. et al., Nucleic Acids Research, 13: (18): 6792, (1985), "RFLP for the Human Apolipoprotein B Gene: IV; MspI".
Priestly, L. et al, Nucleic Acids Research, 13: (18): 6793, (1985), "RLFP for the Human Apolipoprotein B Gene: V; XbaI".

Primary Examiner—Sidney Marantz
Assistant Examiner—Richard Wagner
Attorney, Agent, or Firm—Ciotti & Murashige, Irell & Manella

[57] ABSTRACT

Polymorphisms in genes related to lipid metabolism, specifically apolipoproteins B, CII, E, and apoAIV, have been identified. Presence or absence of these polymorphisms in particular individuals may be correlated with propensity to show symptoms of atherosclerosis. Also thus correlated are two insertion polymorphisms 5' of the insulin gene.

28 Claims, 4 Drawing Sheets

```
                        CTGCCGCTGAGGAGCCCGCCCAGCCAGCCAGGGCCGCGAGGCCGAGGCCAGGCCGCAGCCCA     62
                                         ↓
GGAGCCGCCCCACCGCAGCTGGCGATGGACCCGCCGAGGCCCGCGCTGCTGGCGCTGCTGGCGCTGCCT                       131
                    METAspProProArgProAlaLeuLeuAlaLeuLeuAlaLeuPro
                                            (-20)
                                                    ↓             . . . . . . . . . . . . . . . . . . . .
GCGCTGCTGCTGCTGCTGCTGGCGGGCGCCAGGGCCGAAGAGGAAATGCTGGAAAATGTCAGCCTGGTC                       200
AlaLeuLeuLeuLeuLeuLeuAlaGlyAlaArgAlaGluGluGluMETLeuGluAsnValSerLeuVal
         (-10)                         (1)                         (10)

TGTCCAAAAGATGCGACCCGATTCAAGCACCTCCGGAAGTACACATACAACTATGAGGCTGAGAGTTCC                       269
CysProLysAspAlaThrArgPheLysHisLeuArgLysTyrThrTyrAsnTyrGluAlaGluSerSer
         △          (20)                          (30)             △

AGTGGAGTCCCTGGGACTGCTGATTCAAGAAGTGCCACCAGGATCAACTGCAAGGTTGAGCTGGAGGTT                       338
SerGlyValProGlyThrAlaAspSerArgSerAlaThrArgIleAsnCysLysValGluLeuGluVal
                  (40)                              (50

CCCCAGCTCTGCAGCTTCATCCTGAAGACCAGCCAGTGCACCCTGAAAGAGGTGTATGGCTTCAACCCT                       407
ProGlnLeuCysSerPheIleLeuLysThrSerGlnCysThrLeuLysGluValTyrGlyPheAsnPro
         (60)                          (70)                          (80)

GAGGGCAAAGCCTTGCTGAAGAAAACCAAGAACTCTGAGGAGTTTGCTGCAGCCATGTCCAGGTATGAG                       476
GluGlyLysAlaLeuLeuLysLysThrLysAsnSerGluGluPheAlaAlaAlaMETSerArgTyrGlu
                     (90)                          (100)

CTCAAGCTGGCCATTCCAGAAGGGAAGCAGGTTTTCCTTTACCCGGAGAAAGATGAACCTACTTACATC                       545
LeuLysLeuAlaIleProGluGlyLysGlnValPheLeuTyrProGluLysAspGluProThrTyrIle
                (110)                          (120)

CTGAACATCAAGAGGGGCATCATTTCTGCCCTCCTGGTTCCCCCAGAGACAGAAGAAGCCAAGCAAGTG                       614
LeuAsnIleLysArgGlyIleIleSerAlaLeuLeuValProProGluThrGluGluAlaLysGlnVal
         (130)                         (140)

TTGTTTCTGGATACCGTGTATGGAAACTGCTCCACTCACTTTACCGTCAAGACGAGGAAGGGCAATGTG                       683
LeuPheLeuAspThrValTyrGlyAsnCysSerThrHisPheThrValLysThrArgLysGlyAsnVal
(150)                     (160)                          (170)

GCAACAGAAATATCCACTGAAAGAGACCTGGGGCAGTGTGATCGCTTCAAGCCCATCCGCACAGGCATC                       752
AlaThrGluIleSerThrGluArgAspLeuGlyGlnCysAspArgPheLysProIleArgThrGlyIle
                  (180)                         (190)

AGCCCACTTGCTCTCATCAAAGGCATGACCCGCCCCTTGTCAACTCTGATCAGCAGCAGCCAGTCCTGT                       821
SerProLeuAlaLeuIleLysGlyMETThrArgProLeuSerThrLeuIleSerSerSerGlnSerCys
                (200)                          (210)

CAGTACACACTGGACGCTAAGAGGAAGCATGTGGCAGAAGCCATCTGCAAGGAGCAACACCTCTTCCTG                       890
GlnTyrThrLeuAspAlaLysArgLysHisValAlaGluAlaIleCysLysGluGlnHisLeuPheLeu
         (220)                          (230)                          (240)

CCTTTCTCCTACAAGAATAAGTATGGGATGGTAGCACAAGTGACACAGACTTTGAAACTTGAAGACACA                       959
ProPheSerTyrLysAsnLysTyrGlyMETValAlaGlnValThrGlnThrLeuLysLeuGluAspThr
                 (250)                          (260)
```

FIG.1

```
         -17 EBI cDNA-)                          -10
5'      (Val)Leu Pro Ala Leu Phe Leu Val Leu Leu Val Leu Gly Phe
GGG GGG CTG CTC CCA GCT CTG TTT CTT GTC CTC CTG GTA TTG GGA TTT
             1       10          20          30          40
                   1                                  10
Glu Val Gln Gly Thr Gln Gln Pro Gln Gln Asp Glu Met Pro Ser Pro
GAG GTC CAG GGG ACC CAA CAG CCC CAG CAA GAT GAG ATG CCT AGC CCG
         50          60          70         80
                          20                    oligomer
Thr Phe Leu Thr Gln Val Lys Glu Ser Leu Ser Ser Tyr Trp Glu Ser
ACC TTC CTC ACC CAG GTG AAG GAA TCT CTC TCC AGT TAC TGG GAG TCA
 90         100         110         120         130
    probe
     30                                      40
Ala Lys Thr Ala Ala Gln Asn Leu Tyr Glu Lys Thr Tyr Leu Pro Ala
GCA AAG ACA GCC GCC CAG AAC CTG TAC GAG AAG ACA TAC CTG CCC GCT
140         150         160         170         180

50                                       60
Val Asp Glu Lys Leu Arg Asp Leu Tyr Ser Lys Ser Thr Ala Ala Met
GTA GAT GAG AAA CTC AGG GAC TTG TAC AGC AAA AGC ACA GCA GCC ATG
190         200         210         220         230
                                70
Ser Thr Tyr Thr Gly Ile Phe Thr Asp Gln Val Leu Ser Val Leu Lys
AGC ACT TAC ACA GGC ATT TTT ACT GAC CAA GTT CTT TCT GTG CTG AAG
        240         250         260         270         280
         79
Gly Glu Glu Stop
GGA GAG GAG TAA CAG CCA GAC CCC CCA TCA GTG GAC AAG GGG AGA GTC
        290         300         310         320

CCC TAC TCC CCT GAT CCC CCA GGT TCA GAC TGA GCT CCC CCT TCC CAC
330         340         350         360         370

GTA CGC TCT TGC ATC CTC CTC CCA ACT CTA GCC TGA ATT CTT TTC AAT
380         390         400         410         420

AAA AAA TAC AAT TCA AAA 3'
430            440   n
```

FIG. 2

```
                                                                    Met Lys Val Leu Trp Ala Ala Leu Leu Val Thr Phe Leu
CCCCA GCGGAGGTGA AGGACGTCCT TCCCCAGGAG CCGACTGGCC AATCACAGGC AGGAAG ATG AAG GTT CTG TGG GCT GCG TTG CTG GTC ACA TTC CTC
                   -90                                         -60                                      -30

Ala Gly Cys Gln Ala Lys Val Glu Gln Ala Val Glu Thr Glu Pro Glu Pro Glu Leu Arg Gln Gln Thr Glu Trp Gln Ser Gly Gln Arg
GCA GGA TGC CAG GCC AAG GTG GAG CAA GCG GTG GAG ACA GAG CCG GAG CCC GAG CTG CGC CAG CAG ACC GAG TGG CAG AGC GGC CAG CGC
 1                                                 30                                              60

Trp Glu Leu Ala Leu Gly Arg Phe Trp Asp Tyr Leu Arg Trp Val Gln Thr Leu Ser Glu Gly Val Gln Glu Glu Leu Leu Ser Ser Gln
TGG GAA CTG GCA CTG GGT CGC TTT TGG GAT TAC CTG CGC TGG GTG CAG ACA CTG TCT GAG GGT GTG CAG GAG GAG CTG CTC AGC TCC CAA
                  90                                     120                                     150

Val Thr Gln Glu Leu Arg Ala Leu Met Asp Glu Thr Met Lys Glu Leu Lys Ala Tyr Lys Ser Glu Leu Glu Glu Gln Leu Thr Pro Val
GTC ACC CAA GAA CTG AGG GCG CTG ATG GAC GAG ACC ATG AAG GAG TTG AAG GCC TAC AAA TCG GAA CTG GAA GAA CAA CTG ACC CCG GTA
           180                                     210                                     240

Ala Glu Glu Thr Arg Ala Arg Leu Ser Lys Glu Leu Gln Ala Ala Gln Ala Arg Leu Gly Ala Asp Met Glu Asp Val Cys Gly Arg Leu
GCG GAG ACG CGG GCA CGG CTG TCC AAG GAG CTG CAG GCC GCG CAG GCC CGG CTG GGC GCG GAC ATG GAG GAC GTG TGC GGC CGC CTG
      270                                     300                                     330

Val Gln Tyr Arg Gly Glu Val Gln Ala Met Leu Gly Gln Ser Thr Glu Glu Leu Arg Val Arg Leu Ala Ser His Leu Arg Lys Leu Arg
GTG CAG TAC CGC GGC GAG GTG CAG GCC ATG CTC GGC CAG AGC ACC GAG GAG CTG CGG GTG CGC CTC GCC TCC CAC CTG CGC AAG CTG CGT
   360                                    390                                     420
```

FIG.3-1

```
Lys Arg Leu Leu Arg Asp Pro Asp Asp Leu Gln Lys Arg Leu Ala Val Tyr Gln Ala Gly Ala Arg Glu Gly Ala Arg Gly Leu Ser
AAG CGG CTC CTC CGC GAT CCC GAT GAC CTG CAG AAG CGC CTG GCA GTG TAC CAG GCC GGG GCC CGC GAG GGC GCC CGC GGC CTC AGC
                    450                                 480                                 510
                                                    ├── oligomer probe ──
Ala Ile Arg Glu Glu Arg Leu Gly Pro Leu Val Glu Gly Arg Val Arg Ala Ala Thr Val Gly Ser Leu Ala Gly Gln Pro Geu Gln Glu
GCC ATC CGC GAG GAG CGC CTG GGG CCC CTG GTG GAA GGC CGC GTG CGG GCC GCC ACT GTG GGC TCC CTG GCC GGC CAG CCG CTA CAG GAG
                540                                 570                                 600

Arg Ala Gln Ala Trp Gly Glu Arg Leu Arg Ala Arg Met Glu Glu Ala Arg Leu Arg Thr Arg Asp Arg Leu Asp Glu Val Lys Glu Gln
CGG GCC CAG GCC TGG GGC GAG CTG CGG GCG CGG ATG GAG GAG GCG CGG CTG CGG ACC CGG GAC CGC CTG GAC GAG GTG AAG GAG CAG
                630                                 660                                 690

Val Ala Glu Val Arg Ala Lys Leu Glu Glu Gln Ala Gln Gln Ile Arg Leu Gln Ala Glu Ala Phe Gln Ala Ala Arg Leu Lys Ser Trp Phe
GTG GCG GAG GTG CGC GCC AAG CTG GAG GAG CAG GCC CAG CAG ATA CGC CTG CAG GCC GAG GCC TTC CAG GCC GCT CGC CTC AAG AGC TGG TTC
                720                                 750                                 780

Glu Pro Leu Val Glu Asp Met Gln Arg Gln Trp Ala Gly Leu Val Gln Lys Val Gln Ala Ala Val Gly Thr Ser Ala Ala Pro Val Pro
GAG CCC CTG GTG GAA GAC ATG CAG CGC CAG TGG GCC GGG CTG GTG CAG AAG GTG CAG GCT GCC GTG GGC ACC AGC GCC GCC CCT GTG CCC
                810                                 840                                 870

Ser Asp Asn His ***
AGC GAC AAT CAC TGA ACGCCGAAGC CTGCAGCCAT GCGACCCCAC GCCACCCCGT GCCTCCTGCC TCCGGCGCAGC CTGCAGCGGG AGACCCTGTC CCCGCCCCAG
                900                                 930                                 960                                 990

CCGTCCTCCT GGGGTGGACC CTAGTTTAAT AAAGATTCAC CAAGTTTCAC GC - Poly(A)
                      1020
```

FIG. 3-2 apoAIV-5'
GAATTCCGAGGACCTCTCTGTCAGCTCCCCTGATTGTAGGAGGATCCAGTGTGGCAAGAAACTCC
GCCCAGCAAGCAGCTCAGGATGTTCCTGAAGGCCGTGGTCCTGACCCTGGCCCTGGTGGCTGTCGCCCAGGGCT

```
    Glu Val Ser Ala Asp Leu Thr Arg Val Gln Val Asp Val Leu Thr Gln Gln Val Ala Thr Gln Val Ala Thr Gln Val Val Thr Met Trp Asp Tyr Phe Ser Gln Leu Ser Asn Asn Ala Lys Glu Ala Val Glu His Leu Gln
    GAG GTC AGT GCT GAC CTC ACC CGG GTG CAG GTC GAC GTC CTG ACC CAG CAG GTC GCC ACA GTG GCC ATG TGG GAC TAC TTC AGC CAG CTG AGC AAC AAT GCC AAG GAG GCC GTG GAA CAT CTC CAG
     1                               10                              20                              30                                                                      90

Lys Ser Glu Leu Thr Gln Gln Leu Asn Ala Leu Phe Gln Asp Lys Leu Gly Glu Val Asn Thr Tyr Ala Gly Asp Leu Gln Lys Lys Leu
    AAA TCT GAA CTC ACC CAG CAA CTC AAT GCC CTC TTC CAG GAC AAA CTT GGA GAA GTG AAC ACT TAC GCA GGT GAC CTG CAG AAG AAG CTG
                                                               120                                                     150                                                     180

Val Pro Phe Ala Thr Glu Leu His Glu Arg Leu Ala Lys Asp Ser Glu Lys Leu Lys Glu Ile Gly Lys Leu Glu Leu Arg
    GTG CCC TTT GCC ACC GAG CTG CAT GAA CGC CTG GCC AAG GAC TCG GAG AAA CTG AAG GAG ATT GGG AAG CTG GAG CTG AGG
                     210                                                     240                                                     270

Ala Arg Leu Leu Pro His Ala Asn Glu Val Ser Gln Lys Ile Gly Asp Asn Leu Arg Glu Leu Gln Gln Arg Leu Glu Pro Tyr Ala Asp
    GCC CGG CTG CTG CCC CAT GCC AAT GAG GTG AGC CAG AAG ATC GGG GAC AAC CTG CGA GAG CTT CAG CAG CGA CTG GAG CCC TAC GCG
                     300                                                     330                                                     360

Gln Leu Arg Thr Gln Val Asn Thr Gln Ala Glu Gln Leu Arg Arg Gln Leu Thr Pro Tyr Ala Gln Arg Met Glu Arg Val Leu Arg Glu
    CAG CTG CGC ACC CAG GTC AAC ACG CAG GCC GAG CAG CTG CGG CGC CAG CTG ACC CCC TAC GCA CAG CGC ATG GAG AGA GTG CTG CGG GAG
                     390                                                     420                                                     450

Asn Ala Asp Ser Leu Gln Ala Ser Leu Arg Pro His Ala Asp Glu Leu Lys Ala Lys Ile Asp Gln Asn Val Glu Glu Leu Lys Gly Arg
    AAC GCC GAC AGC CTG CAG GCC TCG CTG AGG CCC CAC GCC GAC GAG CTC AAG GCC AAG ATC GAC CAG AAC GTG GAG GAG CTC AAG GGA CGC
                     480                                                     510                                                     540
```

POLYMORPHISMS RELATED TO LIPID METABOLISM: APOB, APOCII, APOE, APOAIV

This is a continuation-in-part of U.S. Patent Application Ser. No. 869,177, filed 30 May 1986, now abandoned, which is a continuation-in-part of U.S. Patent Application Ser. No. 782,663, filed 30 Sept. 1985, now abandoned.

TECHNICAL FIELD

The invention relates to the use of genetic polymorphisms to determine disease states. More particularly, the invention concerns the use of polymorphisms of the apolipoprotein B, CII, E, and AIV genes to diagnose susceptibilities to atherosclerosis.

BACKGROUND ART

The degree of morbidity and mortality associated with atherosclerosis in developed countries is higher than that associated with any other particular disorder, even cancer. The disorder manifests itself in the form of cholesterol depositon in arterial cell walls. The deposition is slow and irreversible and starts at an early age. Clinical symptoms may take years to manifest themselves and are extremely serious; they include coronary heart disease and stroke. Generally, the disease process will have begun long before these clinical manifestations appear.

Because environmental as well as hereditary factors influence the course of the cholesterol deposition and offer means for at least a mitigation of the process, it is desirable to have available a diagnostic technique which provides an early warning of the onset of the deposition. The present technique depends on measuring cholesterol or triglyceride levels in serum, and while these levels can be measured quite accurately, they do not offer the desirable high correlation to true susceptibility. More reliable predictive methods, which relay on detection of atheromatous lesions, use highly invasive procedures, which are sufficiently painful and expensive that they cannot be employed on a screening basis, or even applied to specific groups selected on the basis of family histories. These techniques also offer too little, too late; by the time the atheromatous lesions have appeared, the most effective time for treatment has been passed.

The importance of early detection is made more poignantly evident by the fact that an effective, but inconvenient and unattractive long term treatment is available— -i.e., lowering serum cholesterol through consistently controlled diet or use of cholestorol-lowering drugs. Resistance to this approach will be encountered unless it is clear that the "deprivation" is warranted. The problem is not what the treatment should be, but to whom the treatment should be applied.

A technique that inherently offers the advantages of early detection, if its results can be effectively correlated with the disorder to be assessed, is genetic analysis. Since the genomic characteristics of an individual are basically determined, it is assumed, at conception, genetic aberrations which are indicia of later metabolic disorders are an ideal early diagnosis tool. Genetic testing can be routinely conducted using present methodology, as early as the seventh week of fetal life. Over the last ten years, the availability of restriction enzymes and DNA probing techniques has made possible the use of "restriction fragment length polymorphisms" (RFLPs) in such diagnosis. Using the, by now, well established Southern blot hybridization technique (Southern, E., *J Mol Biol* (1975) 98:503-517), it has been possible successfully to diagnose sickle cell anemia (Kan, Y. W., et al, *Proc Natl Acad Sci (USA)* (1978) 75:5631); β-thalessemia (Antonarakis, S.E., et al, *Proc Natl Acad Sci (USA)* (1983) 79:137); type II diabetes (Rotwein, P., et al, *Science* (1981) 213:1117); familial growth hormone deficiency (Phillips, J. A., III, *Banbury Report* 14, Cold Spring Harbor Laboratory (1983) pp 305–315); phenylketonuria (Woo, S.L.C., et al, *Nature* (1983) 306:151); Huntington's disease (Gusella, J. F., et al, *Nature* (1983) 306:234); and hemophilia B (Gianelli, et al, *Lancet* (1984) i:239, Grunenbaum, et al. *J. Clin Invest* (1984) 73:1491).

All of the foregoing successes are grounded in identification of a particular polymorphism or polymorphisms which correlates with the disease or disorder in question. It has been calculated that the number of polymorphisms expected in the human genome should be of the order of $10^7$, based on an assumed probability of 0.05 for a given nucleotide to be polymorphic; this number being inferred from studies of the human growth hormone, αI-antitrypsin and β-like globin gene cluster loci (Jeffreys, A. J., *Cell* (1979) 181–10; Oster, H., et al, *Am J. Hum Gen* (1984) 36(suppl) 150S). The challenge is to determine which of these over ten million polymorphisms is associated with a particular disorder, and to devise a procedure to detect it.

The present invention provides polymorphisms located in genes related to lipid metabolism, those encoding apolipoproteins B, CII, E, and AIV, which are useful in predicting susceptibility to atherosclerosis. Other polymorphisms in the apoAI/CIII gene complex also useful in atherosclerosis prediction are disclosed in U.S. Ser. No. 724,192, filed 17 Apr. 1985, and its continuation-in-part application U.S. Ser. No. 782,666, filed 30 Sept. 1985.

DISCLOSURE OF THE INVENTION

The invention provides identification of polymorphisms which are useful as predictors of the subsequent devlopment of atherosclerosis. Since most of these polymorphisms are located in the genomic sequences which regulate lipid metabolism, their pattern of presence or absence correlates to propensity to develop this disease. In addition, the presence or absence of these polymorphisms is useful as a form of genetic identification of fingerprinting of an individual and in ascertaining familial relationships.

Thus, in one aspect, the invention is directed to a method of predicting the likelihood of development of atherosclerosis in an individual, or of genetically identifying said individual, which method comprises detecting one or more of:

the presence or absence of PvuII, StuI, EcoRVa, EcoRVb, EcoRVc, HpaI, or DraI polymorphisms in the apoB gene;

the presence or absence of "BamHI", "BanI", "BgII", or "NcoI" polymorphisms in the apoCII gene;

the presence or absence of the "HpaI" polymorphism in the apoE gene;

the presence or absence of four XbaI polymorphisms in the apoAI/CIII/AIV gene complex detected with the apoAIV probe;

the presence or absence of a "TaqI" polymorphism in the apoAI/CIII/AIV gene complex detected with the apoAIV probe;

the presence or absence of a "DraI" polymorphism in the apoAI/CIII/AIV gene complex detected with the apoAIV probe; and the presence of absence of a "NcoI" polymorphism in the apoAI/CIII/AIV gene complex detected with the apoAIV probe.

In addition, two insertion polymorphisms 5' of the insulin gene, which have been reported by others, have been shown herein to be predictive of atherosclerosis.

Stated in another way, the invention is directed to a method for predicting the susceptibility of an individual to atherosclerosis or of providing genetic identification of said individual by digesting human genomic DNA of an individual subject and detecting one or more of:

the presence or absence of a 5.5 kb PvuII digestion fragment which hybridizes to a 970 bp apoB probe;

the presence or absence of a 5.2 kb StuI fragment which hybridizes to a 2 kb apoB probe;

the presence or absence of a 4.8 kb EcoRV fragment which hybridizes to a 3 kb apoB probe;

the presence or absence of 11.0 and 7.0 kb EcoRV fragments which hybridize to a 3 kb apoB probe;

the presence or absence of 3.6 and 2.7 kb EcoRV fragments which hybridize to a 3 kb apoB probe;

the presence or absence of 8.3 and 6.2 kb HpaI fragments which hybridize to a 3 kb apoB probe;

the presence or absence of a variable 2.3-2.6 kb DraI fragment which hybridizes to a 3 kb apoB probe;

the presence or absence of a 1.2 kb BanI digestion fragment, the presence or absence of a 3.8 kb BglI fragment, the presence or absence of a 5.9 kb BamHI digestion fragment, the presence or absence of a 15.8 NcoI digestion fragment, and the presence or absence of a 17.8 kb NcoI digestion fragment, all hybridizing to the apoCII probe;

the presence or absence of a 5 kb HpaI digestion fragment hybridizing to the apoE probe;

the presence or absence of a 10 kb XbaI digestion fragment hybridizing to the apoAIV probe (the "XbaI-a" polymorphism);

the presence of absence of a 2.0 kb XbaI digestion fragment hybridizing to the apoAIV probe (the "XbaI-b" polymorphism);

the presence or absence of a 20 kb XbaI digestion fragment hybridizing to the apoAIV probe (the "XbaI-c" polymorphism);

the presence or absence of a 4.8 kb XbaI digestion fragment hybridizing to the apoAIV probe (the "XbaI-d" polymorphism);

the presence or absence of a 3.6 kb TaqI digestion fragment hybridizing to the apoAIV probe;

the presence or absence of a 7.4 kb DraI digestion fragment hybridizing to the apoAIV probe; and the presence or absence of a 9.5 kb NcoI digestion fragment hybridizing to the apoAIV probe.

Of course, the presence or absence of the more frequently occurring fragment corresponding to each of the above polymorphisms is also relevant both for predicting susceptibility and for genetic fingerprinting.

In addition, the invention relates to a method to predict the susceptibility of an individual to atherosclerosis by digesting genomic DNA from this individual and detecting the presence or absence of a 600–1600 bp insert or a 1600–2200 bp insert 5' of the insulin gene.

The invention thus relates to determination of a genetic fingerprint of a subject, which fingerprint may relate to disorders of lipid metabolism and transport, using polymorphisms of the genes associated with proteins involved in these functions. The genetic fingerprint is also useful in identification of particular individuals and in assessing familial relationships. The invention is also directed to kits suitable for performing the method of the invention.

BRIEF DESCRIPTION OF THE DRAWINGS

FIG. 1 is the DNA sequence of the apoB (0.97 kb) probe;

FIG. 2 is the DNA sequence of the apoCII probe;

FIG. 3 is the DNA sequence of the apoE probe;

Figure 4A-2:
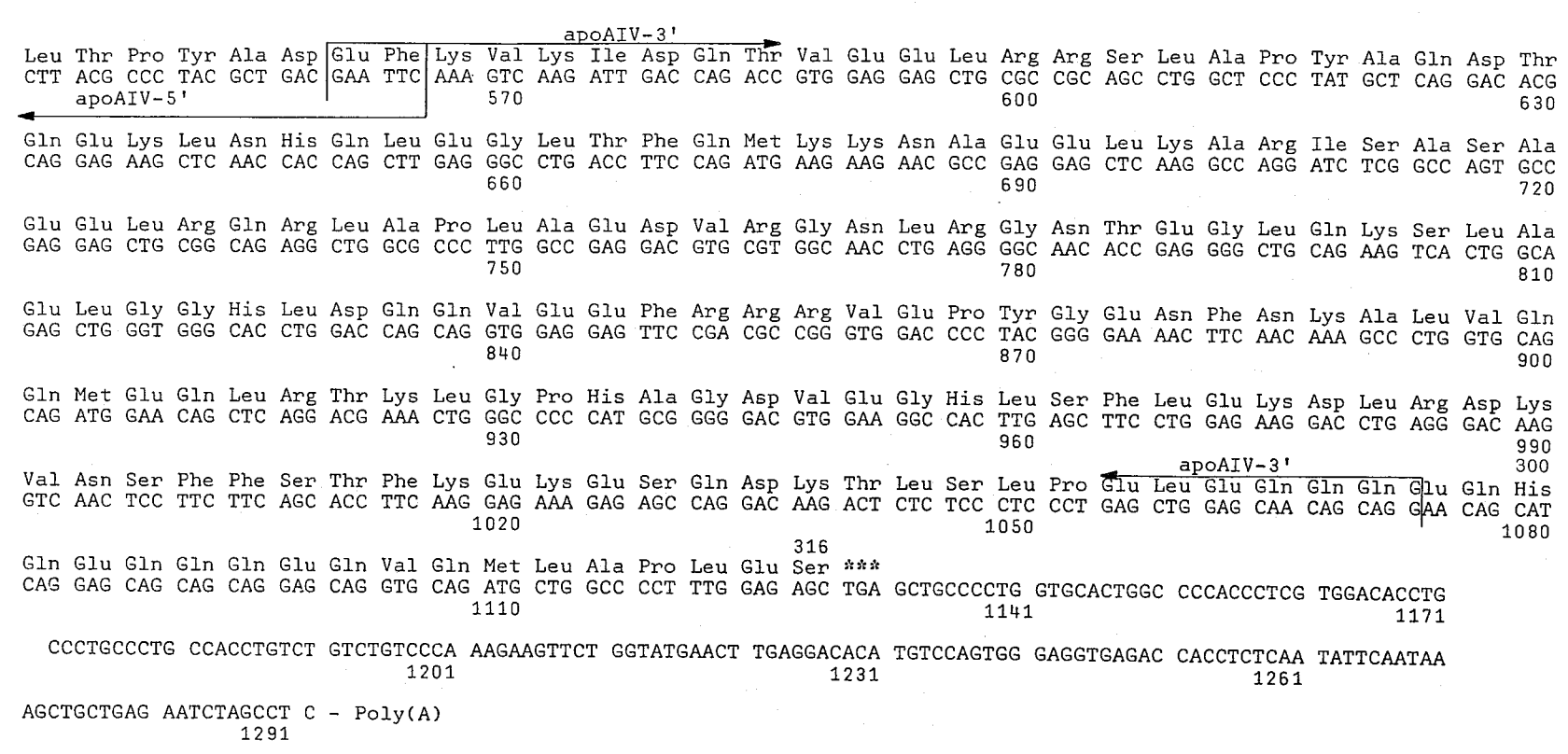

FIG. 4a is the DNA sequence of the two-part apoAIV probe; and

MODES OF CARRYING OUT THE INVENTION

Figure 4B:
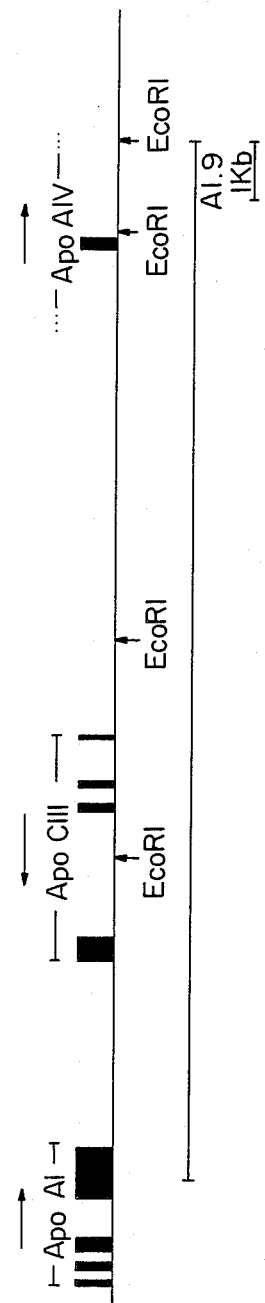
FIG. 4b shows the apoAI/CIII/AIV gene complex.

In the description below, distances of polymorphisms from reference points and lengths of deletions are often given in bp or kb. Where the sequence is known, such measures can be quite precise, but when assessed by measuring fragment sizes on gels or by other experimental means, these measures contain a margin of uncertainty, as is well understood in the art. In general, for measures of >4 kb, the margin of uncertainty is $\pm \sim 0.3$ kb; for smaller lengths, the error is $\pm \sim 10\%$. Thus, the "300 bp" deletion may be slightly larger or smaller, and the 4 kb spacing from the apoAI gene is only approximate.

A. Techniques for Detection of Polymorphisms

Application of the method of the invention to predict potential atherosclerotic individuals or to obtain a genetic "fingerprint" based on some or all of the polymorphisms associated with the designated genomic regions, employs standard techniques of DNA extraction, purification, restriction enzyme digestion, and size separation. Techniques for hybridization with probe and detecting successfully hybridized substrate arranged according to molecular weight are also well known to those in the art. The general approach to finding and detecting the significant polymorphisms is the following:

DNA is extracted from the somatic cells of the individual to be tested, for example from leukocytes, placental cells, cultured fibroblasts, or, in the case of fetal individuals, from cells of the amniotic fluid. The high molecular weight DNA fraction is separated, and subjected to treatment with a particular, selected restriction enzyme, such as, for example, EcoRI, BamHI, MstI, XmnI, and the like. After digestion of the high molecular weight DNA, the digest is applied to a polyacrylamide or agarose gel and subjected to electrophoresis to obtain separation of the DNA fragments resulting from restriction enzyme digestion into positions on the gel determined by the size (length) of the fragment. The contents of the gel are then replicated by transferring to a nitrocellulose filter or other suitable matrix for use as a probe hybridization support. The DNA fragments, either before or after transfer to the nitrocellulose filter replica, are treated with a denaturant such as sodium hydroxide/salt. The denatured, single-stranded DNA, replicated electrophoresis patterns are probed with labeled (usually be $^{32}P$) single-stranded DNA fragments. Other labels besides radioactivity, such as fluorescent molecules may also be used.

Depending on the probe selected, fragments will be detected which derive from a particular region on the genome. For example, in the methods of the invention, a cDNA sequence from the apolipoprotein B (apoB) or apolipoprotein CII (apoCII) or apolipoprotein E (apoE) gene sequences is used as a probe. Therefore, the only fragments which will appear on the hybridized filters are those which contain sequences complementary to the designated probe--i.e., only those which have not been severed either in the genome itself or by the restriction enzyme cleavage from the complementary apoB or apoCII or apoE fragment. Stated in another way, by using a particular probe, alterations in the genome which are proximal to sequences corresponding to that probe are detected.

The specific procedures used in the general process described in the preceding paragraphs are understood in the art. Procedures for DNA extraction from somatic cells may, for example, be found in Kan, Y.W., et al, *Proc Natl Acad Sci (USA)* (1978) 75:5631–5635; Taylor, J.M., et al, *Nature* (1984) 251:392–393; and Kan, Y.W., et al, *N Eng J. Med* (1977) 297:1080–1084. Further improvements which permit rapid extraction of the DNA are also disclosed by Law, D. G., et al, *Gene* (1984) 28:153–158. Techniques for size separation of the restriction enzyme treated DNA fragments are also described in the foregoing references. Restriction enzyme digestions are generally standard in the art and are carried out under buffer. ionic strength, and temperature conditions which are specified by the manufacturer of the particular restriction enzyme.

Transfer to nitrocellulose or other support and probing by prehybridization with nonspecific DNA followed by hybridization with labeled probe are also standard procedures disclosed, for example, in the foregoing references and by Southern, E., (supra). The section of the genome which is fingerprinted or otherwise subject to study using the results is, of course, dependent on the nature of the probe. The probes useful in the present invention are selected from the apoB, apoCII, and apoE genes.

B. Nature of the Probes Useful in the Invention

The fragment pattern obtained is diagnostic for a particular polymorphism if the probe selected is complementary to a DNA sequence sufficiently proximal to the polymorphism on the genome that it is not severed from the polymorphism by the restriction cleavage, and has a low probability of being segregated from the polymorphism by crossing over. Acceptable distance limits between the region of probe complementarity and the polymorphism are therefore arbitrary. Generally, probes which hybridize to DNA sequences within 10 kb upstream or downstream of the polymorphism give acceptable results. Occasionally, the pattern of restriction enzyme cleavage may place a distal probe hybridization site on a fragment irrelevant to the polymorphism. The closer the probe to the polymorphism, the greater the range of usable restriction enzymes. Accordingly, as used herein, a probe which is a "substantial equivalent" to a specified probe is one which gives the same fragment length in digests of DNA from individuals for a particular polymorphism when the same restriction enzyme is used under the same conditions. For example, slightly shorter or longer probes could be used which hybridize to the same region as the designated probe without altering the results; a probe which hybridizes closer to the site of the polymorphism could also be substituted.

Since atherosclerosis is associated with a defect in cholesterol metabolism, in addition to the the apoAI/CIII gene which is associated with regulation of blood plasma cholesterol, as disclosed in U.S. Ser. No. 724,192 (supra), genes encoding other proteins related to lipid metabolism are also useful. The gene regions which are of interest with respect to the polymorphisms herein are those of the apoB, apoCII, apoE, and apoAIV genes.

Apolipoprotein B is the major protein component of very low density lipoproteins (VLDL) and of chylomicrons. It is the sole protein in low density lipoproteins (LDL), and is essential for the assembly and secretion of chylomicrons and VLDL. It also functions as the ligand for removal of LDL from circulation by receptor-mediated uptake into a variety of cells. (Lusis, A. J., et al, *Proc Natl Acad Sci (USA)* (1985) 82:4597–4601.) Four major plasma species of apoB have been described (Kane, J. P., et al, *Proc Natl Acad Sci (USA)* (1980) 77:2465–2469). However, two of these appear to arise from one of the others by virtue of the protease activities found in plasma. (Cardin, A. D., et al, *J Biol Chem* (1984) 259:8522–8528; Yamamoto, M., et al, *J Biol Chem* (1985) 260: 8509–8513). One of the primary forms, apoB-48, is synthesized by the intestine and is a component of chylomicrons; the other primary form, which is apparently attacked by the plasma protease, apoB-100, is the protein ligand on LDL that binds to the LDL receptor and results in uptake and catabolism of LDL by the liver (Deeb, S. S., et al, *Proc Natl Acad Sci (USA)* (1985) 82: 4983–4986). In any event, the apolipoproteins encoded by the apoB gene are integral to cholesterol and fat metabolism. Indeed, it has been shown by others that elevated plasma levels of apoB-100 have been found in individuals with premature coronary artery disease (Brunzel, J. D., et al, *Atherosclerosis* (1984) 4:79–83), and individuals with familial hyperlipidemia and hypercholesterolemia also seem to have elevated levels of this protein (Brunzel, J. D., et al, ibid; Brunzel, J. D., et al, *J Lipid Res* (1983) 24:147–155). At least partly because of this interest, cDNA clones for apoB or portions thereof have been prepared (Deeb, S. S., et al, and Lusis, A. J., et al, both supra; Protter, A. A., et al, *Proc Natl Acad Sci,* in press).

Another apolipoprotein, apoCII, also plays an important role in the relevant metabolic pathways. It is a 79 amino acid peptide associated with the circulating triglyceride-rich lipoproteins, chylomicrons, and VLDL (Myklebost, O., et al, *J Biol Chem* (1984) 7:4401–4404). It is known to activate lipoprotein lipase (LaRosa, J. C., et al, *Biochem Biophys Commun* (1970) 41:57–62; Breckenridge, W. C., et al, *New Eng J. Med* (1978) 298: 1265–1272). There has been reported association with apoCII deficiency, hypertriglyceridemia, and other lipoprotein abnormalities. (Breckenridge, W. C., et al, ibid; Cox, D., et al, *New Eng J Med* (1978) 299: 1421–1424; Yamamura, T., et al, *Atherosclerosis* (1979) 34:53–65; Miller, N. E., et al, *Eur J Clin Invest* (1981) 11: 69–76). cDNA clones encoding this gene have also been prepared (Myklebost, O., supra) and a polymorphism in this gene detectable by digestion with TaqI and probing with an apoCII related probe has been reported by Humphries, F. E., et al, *Mol Biol Med* (1983) 1: 463–471. As reported by Humphries, however, there seems to be no association between this TaqI polymorphism and factors that predispose an individual to hyperlipidemia; these results are confirmed by our work.

A third relevant gene sequence is that encoding human apolipoprotein E. ApoE is also a component of chylomicrons and chylomicron remnants, and is found in VLDL and HDL. The sequence of this 299 amino acid protein is known, and a cDNA clone has been prepared (McLean, J. W., et al, *J Biol Chem* (1984) 25: 6498–6504). ApoE appears to mediate the uptake of lipoproteins through specific receptors (Mahley, et al, *Biochem Biophys Acta* (1983) 737:197–222; Mahley, R. W., *Klin Wochenschr* (1983) 61: 225–232 and to bind to LDL receptors (Innerarity, T. L., Biochemistry (1978) 17: 1440–1447). Variable forms of apoE protein have been found, and certain abnormal forms of apoE2 seem to be associated with a genetically determined hyperlipoproteinemia (Mahley, R., et al, *Adv Intern Med* (1983) 29: 385–411).

A fourth protein whose coding sequence serves as the basis for a useful probe is human apolipoprotein AIV. Genetic mapping has shown that the apoAIV and apoAI/CIII gene regions are, in fact, closely linked (Schamaun, O., et al, *Hum Genet* (1984) 689:181–184; Karathanssis, S. K., *Proc Natl Acad Sci USA* (1985) 82:6374–6378; Elshourbagy, N. A., et al, *J Biol Chem* (1986) 261:1998–2002), and a number of structural and organizational similarities have been noted between the apoAI and apoAIV genes. ApoAIV is a 376 amino acid protein whose complete amino acid sequence is known (Elshourbagy, et al, (supra)). ApoAIV is believed to mediate various metabolic steps associated with cholesterol and other lipid metabolism in a manner similar to apoAI/CIII.

It should be noted that due to the proximity of the apoAI/CIII gene to the apoAIV gene, polymorphisms detected with the apoAIV probe may in fact detect changes in DNA sequence which reside in the apoAI/CIII complex. Therefore, the polymorphisms detected with this probe will be referred to as polymorphisms of the "apoAI/CIII/AIV gene complex". The relative positions and reading directions of these protein encoding regions are shown in FIG. 4b.

In summary, each of the foregoing gene sequences encoding apoB, apoCII, apoE, and apoAIV appear to be intimately involved with the metabolic steps that determine cholesterol and other lipid metabolism, and are thus relevant to prognosis of atherosclerosis. Accordingly, probes designed to hybridize to regions of these genes are useful in the method of the invention.

A description of appropriate probes and restriction enzymes for detection of insertion polymorphisms 5' of the insulin gene is found in Bell, C. I., et al, *Nature* (1980) 284:26–32; *Proc Natl Acad Sci* USA (1981) 78:5759–5763; *Diabetes* (1984) 33:176–183.

Probes are labeled by nick translation using a [$^{32}$P] dCTP and α[$^{32}$P] dGTP, which results in fragmentation of the probe. Thus, cDNA probes which are complementary only to the exon regions of the gene and which span over intron regions are workable in the method of the invention.

C. Kits

The reagents suitable for applying the method of the invention to detect the appropriate polymorphisms may be packaged into convenient kits providing the necessary materials, packaged into suitable containers, and, optionally, suitable containers or supports useful in performing the assay. The essential components of the assay include the restriction enzyme associated with the polymorphism, and a suitable probe. Additionally, packages containing concentrated forms of reagents used for hybridization, prehybridization, DNA extraction, etc. may be included if desired. In particular, however, labeled probe, or reagents suitable to form conveniently labeled probe, are useful in facilitating the conduct of the method of the invention. Instructions regarding the conduct of the method are also included in the kit. Said instructions describe the operations which constitute the assay--i.e., the manner of detecting the relevant genomic fragments and indicating the correlation of results to atherosclerosis prediction.

D. Association of Polymorphisms with Atherosclerosis

It should first be noted that the designation of the more frequently encountered DNA sequences, yielding the more frequently encountered fragment as "normal" has no particular meaning in obtaining correlations to disease. The higher frequency sequence or pattern may correlate with the disease instead of the "polymorphic" or lower frequency sequence or pattern. These results are stated in terms of "normal" and "polymorphic" entirely for convenience.

Polymorphisms in the apoB, apoCII, apoE, and apoAIV regions may be correlated with a propensity to exhibit the symptoms of atherosclerosis. Such correlations are discerned by screening samples of patient and control populations. One useful criterion for separating patients from controls is the presence or absence of atheromatous plaques, as detected by angiography. Thus, a sample population may be divided into those showing atheromatous plaques using this technique and those lacking them. DNA samples are then obtained from the leukocytes or other convenient source of both patient and control groups and subjected to the methods of detecting the relevant polymorphisms, as described herein. Correlations can then be made using any convenient statistical method. One particularly convenient method which results in the calculation of a relative incidence of atherosclerosis is illustrated below. However, any other convenient correlation method may also be used.

There is uncertainty in the literature as to whether a 1600–2200 bp ("U") insertion polymorphism, which has a 0.32 frequency in the population, does (Owenbach, D. B., et al, *Lancet* (1982) 1291–1293; Mandrup-Poulsen, T., *Lancet* (1984) 250–252) or does not (Jowett, N. I., et al, *Lancet* (1984) 348) correlate to atherosclerosis. We find that the "U" insertion correlates well with an increased risk, and that a shorter 600–1600 bp "M" insertion (freq. =0.04) correlates moderately with a decreased risk of atherosclerosis.

E. Examples

The following examples are specific with respect to the probes exemplified and with respect to the precise conditions of DNA extraction, probe hybridization, etc. It is understood that these factors are illustrative but not limiting. The essential features of the invention as it relates to detection of a particular polymorphism are selection of enzyme and probe. For example, in the PvuII/B embodiment for atherosclerosis prediction, one may use PvuII digestion of the genomic DNA and probe with a sequence complementary to the genomic sequence (in the nonrepeating regions) proximal (i.e., in this case within ∼ <5.5 kb) to the site of the polymorphism. Alternatively, other restriction enzymes may be used in conjunction with a probe which hybridizes in particularly close proximity to the polymorphism.

The fingerprinting polymorphisms may employ other specific restriction enzymes. A variety of substantially equivalent probes could be designed with respect to this region, and the particular restriction enzyme and cDNA probe chosen are arbitrary. However, it should be noted, as is understood in the art, that the efficacy of the probe is enhanced as it moves closer to the site of the polymorphism. Otherwise, additional cleavage points may be encountered between the polymorphism and the probe, and also the probing site may be separated from the site of the polymorphism during replication by crossing-over events.

E.1. Procedures for Analysis

Leukocytes were obtained from freshly drawn blood collected from each of the human subjects, and high molecular weight genomic DNA was isolated by the procedure of Law, D. J., et al, *Gene* (1984) 28:153–158.

High molecular weight DNA was divided into portions and each was digested to completion with one of the various restriction enzymes under conditions recommended by the suppliers (New England Biolabs and Bethesda Research Laboratories). The digests were electrophoresed in horizontal agarose gels in 30 mM $NaOH_2PO_4$, 36 mM Tris, 1 mM EDTA, pH 7.7. After electrophoresis, DNA fragments were denatured in situ in 0.5M NaOH/1.5M NaCL for 2×10 min, neutralized in 1M ammonium acetate pH 7.2 for 2×10 min, and transferred overnight onto nitrocellulose paper (Schleicher and Schuell). The filters were rinsed in 2×SSC (1×SSC is 0.15M NaCl, 0.015M sodium citrate pH, 7.4) and baked for 2 hr at 80° C. in vacuo and then were prehybridized for 5 hr in plastic bags using 0.3 ml/cm$^2$ of a solution containing 5×SSPE (1×SSPE is 10 mM Na phosphate pH 7.4, 0.18M NaCl and 1 mM EDTA) containing 5×Denhardt's solution 1×Denhart's contains 0.2 mg/ml each of Ficoll, polyvinyl pyrrolidone and bovine serum albumin), 40% vol/vol) formamide, and 250 μg/ml sheared and denatured salmon sperm DNA, and hybridized overnight in the same bag in 0.1 ml/cm$^2$ of 5×SSPE, 1×Denhardt's solution, 40% (vol/vol) formamide, 10% dextran sulfate, and 100 μg/ml sheared and denatured salmon sperm DNA, mixed with 100 ng per bag (containing 1 or 2 filters) of the appropriate $^{32}$P-labeled probe, as discussed below. Prehybridization and hybridization were performed at 42° C.

Filters were then washed twice at room temperature in 2×SSC and twice at 65° C. in 2x SSC, 1×Denhardt's solution. DNA sequences hybridized to the $^{32}$P-labeled probes were visualized by autoradiography using XAR-5 films (Kodak) and Cronex intensifying screens (Dupont) at −70° C. for 18 hr to 2 days.

Probes related to four specific genes are used in the illustrations below: three apoB probes: apoB (0.97), apoB (2 kb) and apoB (3 kb); apoCII probe; the apoE probe and a two-part, mixed apoAIV probe.

One apoB probe, apoB (0.97 kb), is a 970 bp EcoRI/EcoRI insert fragment which contains 70 bp of 5' untranslated region and 900 bp of sequence encoding the 30 kd protein. This probe, however, does not overlap with either of the published apoB clones described by Deeb, S.S., or Lusis, A. J. (supra). Isolation of the EcoRI fragment used as probe is described by Protter, A.A., et al, *Proc Natl Acad Sci* (USA), (in press), and the complete DNA sequence of this insert is shown in FIG. 1.

Briefly, an approximately 5×10$^5$ member human adult liver cDNA library (where the insert size averaged 1 kb and the inserts are ligated into the EcoRI site of λgt10) was prepared by the method of Huynh, T., et al, *DNA Cloning Techniques: A Practical Approach* (1984), Grover, D., ed., IRL Press, Oxford. For screening, 9×10$^5$ plaques propagated in C600 (HFL) cells are transferred to replica nitrocellulose filters and processed as described by Seilhamer, J. J., et al, *DNA* 3:309 (1984). The filters are prewashed for 2 hr in 3×NaCl/Cit (1×NaCl/Cit is 150 mM NaCl/15 mM sodium citrate, pH 7.0), 0.1% SDS at 55° C., and then prehybridized in 6×NaCl/Cit, 200 μg/ml denatured salmon sperm DNA, 5×Denhardt's, 0.05% sodium pyrophosphate for 1 hr at 50° C.

A 192-fold degenerate 23 base oligonucleotide probe which encodes, taking account of codon redundancy, the first 8 amino acids of the previously determined sequence of apoB-26 (Asp-Glu-Pro-Pro-Gln-Ser-Pro-Trp) was used as a probe. The probe was 5' end labelled with T4 polynucleotide kinase (PL Biochemicals) and γ-[$^{32}$P]-ATP, added to the filters and incubated for 14 hr at 50° C. The filters were washed twice at room temperature in 5×NaCl/Cit, 0.1% SDS, 0.05% sodium pyrophosphate for 15 min and once at 50° C. for 20 min, dried and autoradiographed with intensifying screens.

One positive plaque, designated LB25-1, was purified and the cDNA insert was subcloned in both orientations into M13/mp8 for sequencing. The EcoRI insert was subcloned into pBR322 to obtain pB25-1 for amplification. pB25-1 thus contains some 5' untranslated region, the signal sequence, and the first 266 amino acids of the mature protein, i.e., apoB (0.97kb) probe.

For the remaining two apoB probes, additional portions of the apoB encoding sequence were obtained using linearized denatured pB25-1 insert as initial probe. A 2×10$^5$ member human adult intestine cDNA library in λgt10 was screened using this insert and a cDNA designated IB7, containing an approximately 1.3 kb insert, about 800 bp of which extended beyond the 3' end of clone pLB25 was obtained. Isolated, denatured IB7 insert was subcloned into pBR322 for amplification, creating pIB7. The purified IB7 insert was denatured and used to screen the intestine library. One positive cDNA fragment designated I10 contained an approximately 3 kb insert, about 2.5 kb of which extended beyond the 3' end of IB7. This cDNA insert was subcloned into the EcoRI site of pBR322, creating pB10. This insert provded the second apoB probe and was designated apoB (3 kb).

Linearized, denatured pB10 insert was used as a probe to obtain still another cDNA fragment designated IB-(2)1, containing an approximately 2 kb insert, about 1 kb of which extends in the 3' direction beyond the IB-10 sequence. The EcoRI cDNA insert was also subcloned into the EcoRI site of pBR322, creating pB(2)1. This insert represents the third apoB probe and is designated apoB (2kb).

The apoCII probe is a 1.03 kb EcoRI/EcoRI insert fragment which corresponds to a portion of the Myklebost cDNA (supra). This fragment was obtained from a human fetal liver cDNA library constructed in λgt-10 (by providing EcoRI linkers and inserting into the EcoRI site of the phage) and screened with a 51 base synthetic oligonucleotide containing the coding sequence of nucleotides 73–122 as published by Myklebost. Two positive clones were obtained from 500,000 screened, and one was sequenced; it spans nucleotides 10–432 encompassing amino acid −14 of the signal sequence through 38 bases of the 3' untranslated region. The complete sequence of this probe (without the linkers) is shown in FIG. 2.

The apoE probe is a 1 kb EcoRI/EcoRI fragment which covers the entire mature protein-encoding sequence and corresponds to the sequence published by McLean et al, supra. It was obtained from a human fetal liver cDNA library prepared in λgt-10 (by providing EcoRI linkers and inserting into the EcoRI site of the phage) and screened with a synthetic 46 base oligonucleotide containing the coding sequence of nucleotides 469-514 of the published DNA sequence. Of 10 positives obtained from 450,000 phage, one was sequenced and encloses the protein spanning nucleotides −14 to +1020, which encompasses amino acid −4 of the signal sequence through 120 bases of the 3' untranslated region. The complete sequence of this probe (without the linkers) is shown in FIG. 3.

The apoAIV probe is a mixture of two DNA segments which together encode most of the apoAIV protein. The complete sequence of these "apoAIV-5'" and "apoAIV-3'" probes is shown in FIG. 4a. The apoAIV-5' probe extends past the N-terminus of the protein encoding sequence with the additional sequence there shown. It slightly overlaps the 5' end of the apoAIV-3' probe which extends from the codon for amimo acid 187 through part of the codon for amino acid 358, only 18 amino acids short of the C-terminus of the protein. These probes were used as a mixture and are collectively called "apoAIV".

The apoAIV probes were prepared starting with the λA1.9 genomic clone described by Protter, A. A., et al, DNA (1984) 3:449-456. λA1.9 was digested with EcoRI and a 1.2 kb fragment containing a portion of the apoAIV gene was isolated by electrophoresis. The identity of the 1.2 kb fragment was confirmed to correspond to the coding sequence for the apoAIV protein. The 1.2 kb fragment was labeled by nick translation and used to screen a human intestinal cDNA library (human jejunum) in λgt-10 containing about $3 \times 10^5$ recombinant and stored in CsCl. The 661 bp apoAIV-5' probe and the 513 bp apoAIV-3' probe hybridized to the labeled 1.2 kb fragment.

Each of the foregoing probes was labeled to a specific activity of $2-5 \times 10^8$ cpm per μg by nick translation using the BRL nick translation kit (Bethesda Research Laboratories) under recommended conditions with [$^{32}$P] dGTP and [$^{32}$P] dCTP (800 Ci/mmole; Amersham Corporation) in the presence of unlabeled dATP and dTTP. The probe was denatured just before hybridization by incubation for 5 min in a boiling water bath, followed by rapid cooling in ice water.

E.2. Detection and Assay of Polymorphisms

Using the ApoB, ApoCII, ApoE or apoAIV probes in the procedure of paragraph A, a number of polymorphisms were found in the appropriate genomic region. These polymorphisms are summarized in Table 1.

(The normal patterns for EcoRV, HpaI, and DraI digestion and followed by probing with apoB (3 kb) contain multiplicities of fragments. The results shown in the table are only those which distinguish the "normal" from polymorphic individuals.)

The polymorphisms were tested for correlation with the risk of atherosclerosis. To determine these correlations, control and patient groups were set up using as a criterion positive or negative results relating to atheromatous plaque formation as determined by angiography. Persons were classified as "patients" who showed plaques in this assay, whether or not they had suffered heart attacks. They were designated "controls" if the results of this test were negative; none of these persons had had heart attacks.

In interpreting the results, a standard $\chi$-squared analysis was used to determine a significance level. The significance level represents the probability that an association is due to chance alone. Therefore, the results obtained would not hold up if high numbers of subjects were used or a large number of independent trials were made. For example, a significance level of less than 0.05 means that there is a greater than 95% probability that the observed results are true—i.e., that the tested hypothesis is different from the null hypothesis. Therefore it is likely that testing additional or larger numbers of subjects would yield the same results. A significant level of 0.10 means that there is one chance in 10 that the results would be different if a larger or different sample were tested.

TABLE 1

| Polymorphism | Location of Polymorphism | Probe | Enzyme | Fragment Size (kb) "Normal" | Polymorphic | Freq.** |
|---|---|---|---|---|---|---|
| PvuII/B | unk | apoB (0.97 kb) | PvuII | 7.9 | 5.5 | 0.07 |
| StuI/B | unk | apoB (2 kb) | StuI | 5.9 | 5.2 | 0.01 |
| EcoRVa/B | unk | apoB (3 kb) | EcoRV | — | 4.8 | 0.05 |
| EcoRVb/B | unk | apoB (3 kb) | EcoRV | 18.0 | 11.0,7.0 | 0.1 |
| EcoRVc/B | unk | apoB (3 kb) | EcoRV | — | 3.6,2.7 | 0.1 |
| HpaI/B | unk | apoB (3 kb) | HpaI | 8.3,6.2 | — | 0.15 |
| DraI/B | unk | apoB (3 kb) | DraI | — | 2.3-2.6 | 0.5 |
| BamHI/CII | unk | apoCII | BamHI | 4.8 | 5.9 | 0.016 |
| BanI/CII | unk | apoCII | BanI | 2.6 | 1.2 | 0.33 |
| BglI/CII | unk | apoCII | BglI | 3.5 | 3.8 | 0.01 |
| NcoI/CII(15.8) | unk | apoCII | NcoI | 11.5 | 15.8 | 0.2 |
| NcoI/CII(17.8) | unk | apoCII | NcoI | 11.5 | 17.8 | 0.06 |
| TaqI/CII* | 2 kb 3' of apoCII gene | apoCII | TaqI | 3.8 | 3.5 | 0.44 |
| HpaI/E | unk | apoE | HpaI | 3 | 5 | 0.4 |
| XbaI-a/AIV | unk | apoAIV | XbaI | 22 | 10 | 0.23 |
| XbaI-b/AIV | unk | apoAIV | XbaI | 1.8 | 2.0 | 0.20 |
| XbaI-c/AIV | unk | apoAIV | XbaI | 22 | 20 | 0.01 |
| XbaI-d/AIV | unk | apoAIV | XbaI | 22 | 4.8 | 0.06 |
| TaqI/AIV | unk | apoAIV | TaqI | 2.0 1.6 | 3.6 | 0.06 |
| DraI/AIV | unk | apoAIV | DraI | 7.8 | 7.4 | 0.01 |

TABLE 1-continued

| Polymorphism | Location of Polymorphism | Probe | Enzyme | Fragment Size (kb) "Normal" | Fragment Size (kb) Polymorphic | Freq.** |
|---|---|---|---|---|---|---|
| NcoI/AIV | unk | apoAIV | NcoI | 12 | 9.5 | 0.01 |

*This polymorphism has been shown by others and does not form part of the invention.
**Frequency is determined as follows: Each individual has two copies of each chromosome; therefore, at any locus or position on the chromosome each person has two "alleles". If these two alleles are identical, the individual is "homozygous" at this locus; if the two alleles are different, he is heterozygous at this locus. Genetic variation between populations can be quantified using the concept of allele frequency, the proportion of all alleles in a population at the locus that are a particular allele. The frequency of any particular allele in a sample is therefore equal to twice the number of homozygotes for that allele plus the number of heterozygotes for that allele divided by two times the number of individuals in the sample.

The findings were interpreted in terms of the relative risk of persons having the polymorphism to show the disease, compared to those having an absence of the polymorphism. These "odd ratios" by statisticians were calculated according to Wolf, B., *Ann Hum Genet* (1955) 19:251. As applied to the assays below, the relative incidence was calculated as equal to:

$$(PP \times CN/PN \times CP$$

where
PP is the number of patients having the polymorphism;
PN is the number of patients not having the polymorphism;
CP is the number of controls having the polymorphism;
CN is the number of controls not having the polymorphism.

The value calculated by this ratio, if greater than 1, indicates that the persons having the polymorphism are at a greater risk of having the disease; a value less than 1 shows protection against the disease.

Applying this analysis, the TaqI/CII polymorphism reported by others appears to have no correlation. The BanI/CII polymorphism appears to exert a protective effect. For the TaqI/CII polymorphism, 28 of 41 patients, or 68%, exhibited the polymorphism; 12 of 18, or 67%, of controls exhibited it, leading to a calculated relative incidence of 1.07, almost the same risk as for those with no polymorphism. On the other hand, for the BanI/CII polymorphism, 19 of 35 patients, or 54%, had the polymorphism, whereas 3 of 5, or 60%, of controls showed this "abnormality". This leads to a calculated relative incidence value of 0.8 for a slightly protective effect. While the significance level (0.6) is unfavorable, there is still an appreciable probability that this ratio will be maintained upon further testing.

Similarly, the L, M, and U insertion polymorphisms 5' of the insulin gene reported by others (supra) were evaluated. The "U" insertion was found to have a relative incidence of 3.0--a clear correlation with higher risk--while the "M" insertion, with a relative incidence of 0.6, was moderately productive.

Concluding Remarks

Several of the approximately 10 million polymorphisms existent in the human genome have been shown to be useful predictors of individuals at risk for atherosclerosis. These polymorphisms are detectable as fragments of predictable size obtained by digestion of the genomic DNA of the subject individual with a specified restriction enzyme and probing with specific DNA sequences herein described. The availability of this tool for early diagnosis of individuals at risk for atherosclerosis permits the early application of therapeutic measures to prevent the fatal symptomology of the disease.

I claim:
1. A method for determining the genetic identity of an individual human subject which comprises:
    extracting DNA from the somatic cells of the individual human subject to be tested;
    digesting the extracted DNA with a selected restriction enzyme; and
    examining said digested DNA for polymorphisms selected from the group consisting of PvuII/B (5.5), StuI/B (5.2), EcoRVa/B (4.8), EcoRVb/B (7.0), EcoRVb (11.0), EcoRVc/B (2.7), EcoRVc/B (3.6), HpaI/B(6.2), HpaI/B (8.3), DraI/B (2.3-2.6), BamHI/CII (5.9), BanI/CII (1.2), BglI/CII (3.8), NcoI/CII (15.8), NcoI/CII (17.8), HpaI/E (5), XbaI-a/AIV (10), XbaI-b/AIV (2.0), XbaI-c/AIV (20), XbaI-d/AIV (4.8), TaqI-/AIV (3.6), DraI/AIV (7.4), and NcoI/AIV (9.5), wherein said polymorphisms are defined by the presence or absence of a DNA fragment of known length which hybridizes to apoB probe or its substantial equivalent, apoCII probe or its substantial equivalent, apoE probe or its substantial equivalent, or apoAIV probe or its substantial equivalent.

2. The method of claim 1 wherein the restriction endonuclease is PvuII, the probe is apoB 0.97 kb) or its substantial equivalent, and the DNA fragment is 5.5 kb.

3. The method of claim 1 wherein the restriction endonuclease is StuI, the probe is apoB (2 kb) or its substantial equivalent, and the DNA fragment is 5.2 kb.

4. The method of claim 1 wherein the restriction endonuclease is EcoRv, the probe is apoB (3 kb) or its substantial equivalent, and the DNA fragment is 4.8 kb.

5. The method of claim 1 wherein the restriction endonuclease is EcoRv, the probe is apoB (3 kb) or its substantial equivalent, and the DNA fragmeents are 11.0 kb and 7.0 kb.

6. The method of claim 1 whrein the restriction endonuclease is EcoRv, the probe is apoB (3 kb) or its substantial equivalent, and the DNA fragments are 3.6 kb and 2.7 kb.

7. The method of claim 1 wherein the restriction endonuclease is HpaI, the probe is apoB (3 kb) or its substantial equivalent, and the DNA fragments are 8.3 kb and 6.2 kb.

8. The method of claim 1 wherein the restriction endonuclease is DraI, the probe is apoB (3 kb) or its substantial equivalent, and the DNA fragment is 2.3–2.6 kb.

9. The method of claim 1 wherein the restriction endonuclease is BamHI, the probe is apoCII or its substantial equivalent, and the DNA fragment is 5.9 kb.

10. The method of claim 1 wherein the restriction endonuclease is BanI, the probe is apoCII or its substantial equivalent, and the DNA fragment is 1.2 kb.

11. The method of claim 1 wherein the restriction endonuclease is BglI, the probe is apoCII or its substantial equivalent, and the DNA fragment is 3.8 kb.

12. The method of claim 1 wherein the restriction endonuclease is NcoI, the probe is apoCII or its substantial equivalent, and the DNA fragment is 15.8 kb.

13. The method of claim 1 wherein the restriction endonuclease is NcoI, the probe is apoCII or its substantial equivalent, and the DNA fragment is 17.8 kb.

14. The method of claim 1 wherein the restriction endonuclease is HpaI, the probe is apoE or its substantial equivalent, and the DNA fragment is 5 kb.

15. The method of claim 1 wherein the restriction endonuclease is XbaI, the probe is apoAIV or its substantial equivalent, and the DNA fragment is 10 kb.

16. The method of claim 1 wherein the restriction endonuclease is XbaI, the probe is apoAIV or its substantial equivalent, and the DNA fragment is 2.0 kb.

17. The method of claim 1 wherein the restriction endonuclease is XbaI, the probe is apoAIV or its substantial equivalent, and the DNA fragment is 20 kb.

18. The method of claim 1 wherein the restriction endonuclease is XbaI, the prove is apoAIV or its substantial equivalent, and the DNA fragment is 4.8 kb.

19. The method of claim 1 wherein the restriction endonuclease is TaqI, the prove is apoAIV or its substantial equivalent, and the DNA fragment is 3.6 kb.

20. The method of claim 1 wherein the restriction endonuclease is DraI, the prove is apoAIV or its substantial equivalent, and the DNA fragment is 7.4 kb.

21. The method of claim 1 wherein the restriction endonuclease is NcoI, the prove is apoAIV or its substantial equivalent, and the DNA fragment is 9.5 kb.

22. A kit for determining the genetic identity of an individual human subject which comprises at least one probe selected from the group consisting of apoB, apoCII, apoE, and apoAIV and at least one restriction enzyme;
- selected from the group consisting of EcoRV, HpaI, and DraI when apoB is included;
- selected from the group consisting of BamHI, BanI, BglI, and NcoI, when apoCII is included,
- is Hpa I when apoE is included, and is selected from the group consisting of XbaI, TaqI, DraI and NcoI, when apoAIV is included,
- along with instructions for conducting the assay and interpreting results.

23. The kit of claim 22 wherein the DNA probe is apoB (0.97 kb) probe or its substantial equivalent and the restriction endonuclease is PvuII.

24. The kit of claim 22 wherein the DNA probe is apoB (2 kb) probe or its substantial equivalent and the restriction endonuclease is StuI.

25. The kit of claim 22 wherein the DNA probe is apoB (3 kb) probe or its substantial equivalent and the restriction endonuclease is selected from the group consisting of EcoRV, HpaI, and DraI.

26. The kit of claim 22 wherein the DNA probe is apoCII probe or its substantial equivalent and the restriction endonuclease is selected from the group consisting of BamHI, BanI, BglI, and NcoI.

27. The kit of claim 22 wherein the DNA probe is apoE probe or its substantial equivalent and the restriction endonuclease is HpaI.

28. The kit of claim 22 wherein the DNA probe is apoAIV probe or its substantial equivalent and the restriction endonuclease is selected from the group consisting of XbaI, TaqI, DraI and NcoI.

* * * * *